United States Patent [19]

van Andel

[11] Patent Number: Plant 5,542

[45] Date of Patent: Aug. 27, 1985

[54] ALSTROEMERIA NAMED STALTANG

[75] Inventor: Jacob van Andel, Aalsmeer, Netherlands

[73] Assignee: B. V. Handelskwekerij, M.C. van Staaveren, Aalsmeer, Netherlands

[21] Appl. No.: 522,313

[22] Filed: Aug. 11, 1983

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Charles W. Rummler

[57] ABSTRACT

A new cultivar of alstroemeria particularly distinguished by the distinctive magnolia purple color of its flowers and its habit of blooming continuously through the early Spring and early Fall blooming seasons, the flowers being very large in size and borne on strong straight stems of the umbel form of its inflorescence. This plant has a vigorous, strong and upright growth habit, has a medium quantity of foliage and carries its inflorescence at a height of about one and one-half meters where the stalk branches to provide the umbel form of its flower bearing stems.

1 Drawing Figure

BACKGROUND OF THE NEW PLANT

This new variety of alstroemeria originated as a seedling resulting from my crossing of two identified plants growing among a field of breeding stock maintained at Aalsmeer, Holland, for developmental purposes. I discovered this plant among a group of seedlings produced as aforesaid and selected it for propagation and test because of its very lovely and unusual coloring of the influorescence and its apparently profuse blooming habit. I reproduced this plant at Aalsmeer by division of the tubers generated by the tuber from which the stem or stalk of the discovery plant arose and I continued propagation of this new variety through successive generations by root division which has demonstrated that the distinctive characteristics and habits of the discovery plant are retained from generation to generation and appear to be firmly fixed.

DESCRIPTION OF THE DRAWING

My new alstroemeria hybrid is illustrated by the accompanying full color photographic drawing which shows the color characteristics of the inflorescence and the umbel form of its display, the color rendition being as nearly true as it is reasonably possible to obtain by conventional professional photographic procedures.

DESCRIPTION OF THE NEW PLANT

The following is a detailed description of my new alstroemeria cultivar with color designations according to The R.H.S. Colour Chart of The Royal Horticultural Society of London, England.

THE PLANT

Origin: Seedling.

Parentage:

*Seed parent.*—Breeding Stock Plant No. 6089-2.

*Pollen parent.*—Breeding Stock Plant No. 2171-1.

Classification: Hybrid Alstroemeria.

Form: Tall, erect bush having a slender flowering stalk with flower bearing branches in simple umbel arrangement at its top.

Height: About 1.7 meters.

Growth: Vigorous, strong and upright.

Root stock: Tuberous, the tubers bearing many buds from which the flower stems or canes grow in various stages of development during the year.

Foliage:

*Quantity.*—Medium, with 20 to 30 leaves per stem.

*Leaf size.*—Various, depending upon season.

*Leaf shape.*—Elliptic.

*Texture.*—Leathery.

*Color.*—Upper side — Dark Green. Under side — Grey Green.

Rizomes: Number and size varying with season.

*Color.*—White.

THE BUD

Form: Pear-shaped.

Size: Medium.

*Diameter.*—15 to 20 mm.

*Length.*—About 45 mm.

Rate of opening: Normal.

*Character.*—This bud has no calyx. The six petals of the flower are a perianth and divide simultaneously.

Peduncle:

*Length.*—About 3 to 3½ cm.

*Character.*—Peduncle extends from the flower stem at an angle of about 30°.

THE FLOWER

Blooming habit: Continuous and profuse throughout the early Spring and early Fall blooming seasons.

Flower size: Very large.

*Diameter.*—About 7 cm.

*Depth.*—About 6 cm.

Shape: Generally funnel-like.

Borne: Singly on long, strong, umbel stems or branches.

Petalage:

*Number of petals.*—Six arranged in two concentric rings of three.

*Form.*—Broad ovate.

*Texture.*—Soft.

*Appearance.*—Shiny.

*Color.*—Outer petals: Body — R.H.S. 70B (HCC 031/1). Reverse side — R.H.S. 70B (HCC 031/1). Inside petals: Body — R.H.S. 70B. It will be noted that although the inside petals have a somewhat darker shade of coloring than the outer petals, the entire surface of all of the petals bears many longitudinally extending pencil stripes of the same color, R.H.S. 59A/B. The pale blotch on the inside petals is R.H.S. 155A.

Character of main stem or cane:

*Length.*—About 1.7 cm.

*Character.*—Strong and upright.

*Color.*—Dark Green.

Persistence: The flowers hang on and dry.

Lasting quality:

*On the plant.*—About 15 to 20 days.

*As a cut flower.*—About 10 to 15 days.

REPRODUCTIVE ORGANS

Stamens:

*Number.*—Six.

*Arrangement.*—One opposite each petal.

*Anthers.*—Size: About one centimeter. Color: Grey/Brown.

*Filaments.*—Length: About 4 cm. Color: White/-Pink.

*Pollen.*—Color: Blue.

Pistils:

*Number.*—One.

*Style.*—Length: About 8 to 10 mm. Color: Pink.

*Stigma.*—Color: Pink.

This plant is particularly characterized by its flowers, the petals of which have a generally magnolia purple color with the overall surface bearing pencil stripes of lilac purple. The attractive coloration of the inflorescence of this new plant provides an interesting and novel addition to the range of alstroemeria colors.

I claim:

1. A new and distinctive alstroemeria hybrid, substantially as herein shown and described, characterized by the generally magnolia purple coloration of its very large and profusely blooming flowers.

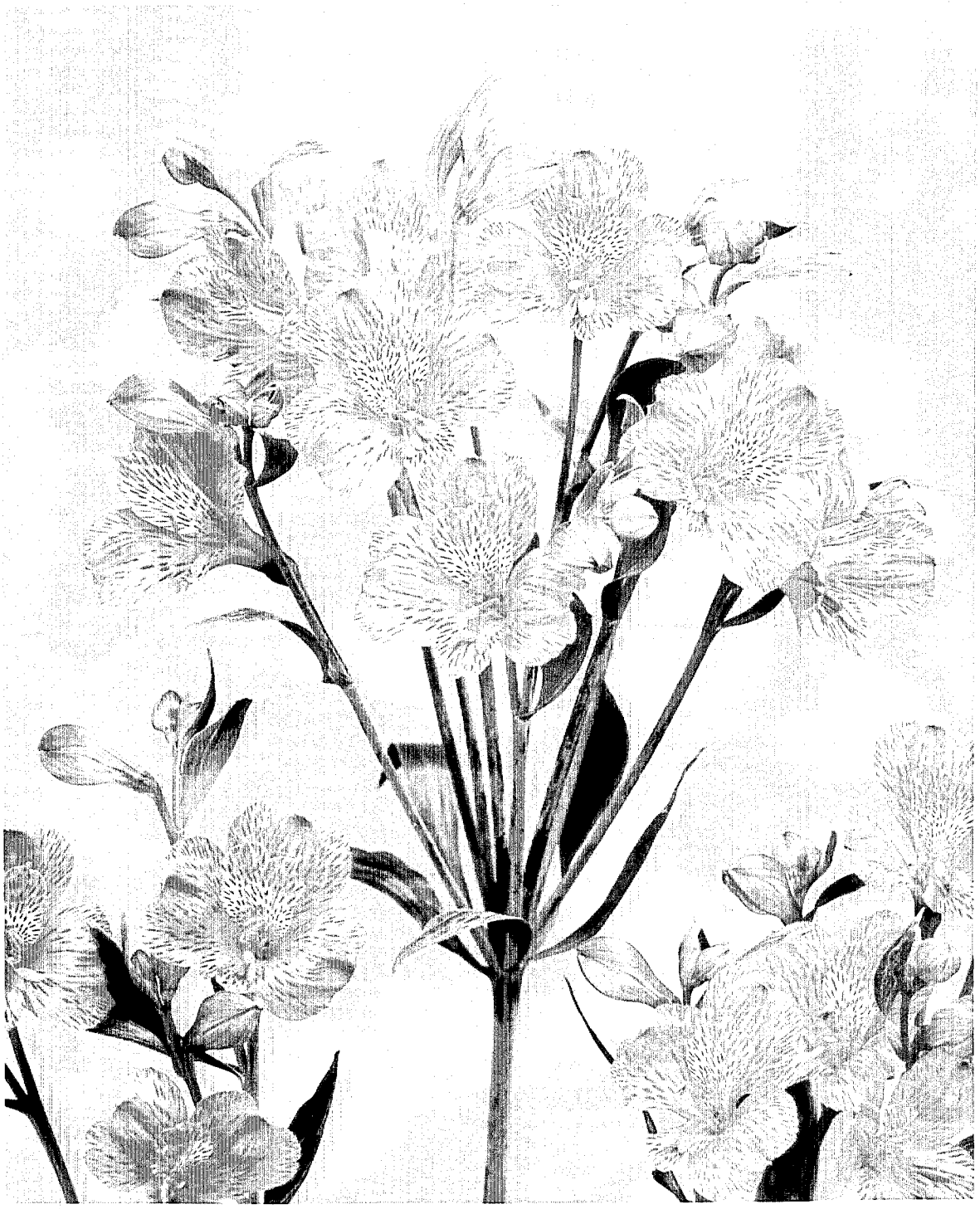

* * * * *